(12) United States Patent
Fischer et al.

(10) Patent No.: US 8,057,749 B2
(45) Date of Patent: Nov. 15, 2011

(54) DEVICE FOR CARRYING OUT CHEMICAL REACTIONS

(75) Inventors: Achim Fischer, Aschaffenburg (DE); Harald Heinzel, Altenstadt-Oberau (DE); Christoph Weckbecker, Gruendau-Lieblos (DE); Klaus Huthmacher, Gelnhausen (DE)

(73) Assignee: Evonik Degussa GmbH, Essen (DE)

( * ) Notice: Subject to any disclaimer, the term of this patent is extended or adjusted under 35 U.S.C. 154(b) by 342 days.

(21) Appl. No.: 12/088,864

(22) PCT Filed: Sep. 18, 2006

(86) PCT No.: PCT/EP2006/066471
§ 371 (c)(1), (2), (4) Date: Apr. 1, 2008

(87) PCT Pub. No.: WO2007/045531
PCT Pub. Date: Apr. 26, 2007

(65) Prior Publication Data
US 2008/0253926 A1 Oct. 16, 2008

(30) Foreign Application Priority Data
Oct. 15, 2005 (DE) .......... 10 2005 049 457

(51) Int. Cl.
*B01J 8/02* (2006.01)
*B01J 35/02* (2006.01)
*B01J 19/00* (2006.01)
*B01J 8/00* (2006.01)
*B01J 10/00* (2006.01)
*B01J 8/04* (2006.01)
*B01J 19/30* (2006.01)

(52) U.S. Cl. ........ 422/211; 422/129; 422/187; 422/198; 422/600; 422/631; 422/632; 422/633; 422/634; 422/635; 422/642; 422/644; 422/654; 422/655

(58) Field of Classification Search .......... 422/129, 422/211, 187–190, 197, 198, 200, 201, 600, 422/630–635, 642, 644, 654, 655
See application file for complete search history.

(56) References Cited

U.S. PATENT DOCUMENTS

| | | | |
|---|---|---|---|
| 4,594,227 A * | 6/1986 | Ohsaki et al. ............... | 422/148 |
| 5,130,098 A * | 7/1992 | Zardi et al. ................. | 422/148 |
| 5,362,454 A | 11/1994 | Cizmer et al. | |
| 6,916,453 B2 * | 7/2005 | Filippi et al. ............... | 422/198 |
| 2002/0088613 A1 * | 7/2002 | Filippi et al. ............... | 165/182 |

FOREIGN PATENT DOCUMENTS

| | | |
|---|---|---|
| EP | 0 194 067 | 9/1986 |
| EP | 0 214 432 | 3/1987 |
| EP | 386692 A2 * | 9/1990 |
| EP | 0 841 301 | 5/1998 |
| GB | 551 312 | 2/1943 |
| JP | 2001038195 A * | 2/2001 |

OTHER PUBLICATIONS

English Translation of JP 2001-038195 A, which was published Feb. 13, 2001.*

* cited by examiner

*Primary Examiner* — Walter Griffin
*Assistant Examiner* — Natasha Young
(74) *Attorney, Agent, or Firm* — Oblon, Spivak, McClelland, Maier & Neustadt, L.L.P.

(57) ABSTRACT

A device for carrying out exothermal chemical reactions wherein a gas phase is guided across a fixed bed and allowed to react, comprising a housing and an exchangeable unit wherein the reaction takes place.

19 Claims, 3 Drawing Sheets

DEVICE FOR CARRYING OUT CHEMICAL REACTIONS

The invention relates to a device for carrying out chemical reactions, in particular for carrying out exothermic and highly exothermic reactions in which a gas phase is passed over a solid material bed and brought to reaction.

Highly exothermic reactions are generally carried out in tube-bundle reactors using a heterogeneous catalyst. There are numerous examples of this in the literature: according to EP 0 188 532 (Nippon Kayaku) or JP 11080052 (To a Gosei Chemical Industry Co.), tube-bundle reactors are used for reacting propene to give acrolein and acrylic acid. According to DE 102 60 094 (BASF AG), tube-bundle reactors are likewise used for producing cyclic diisocyanates.

Reactors of this type, however, are not very flexible in use. For instance, inter alia, the tube number of the reactor establishes the nominal capacity of the reactor. Although this can be reduced by appropriate closure of individual tubes, increasing the nominal capacity, however, is not possible without greater expenditure.

The objects of the invention are to provide a flexibly usable reactor. This is taken to mean that, for example, a changing reaction performance over the lifetime of the catalyst can make adaptation of the reaction surface necessary. Likewise it could be expedient to exchange tubes, for example, for one or more stages or for plates. Also, cleaning, maintenance work or change of catalyst force downtimes in a conventional tube-bundle reactor which cause high costs due to the loss of production capacity.

To counteract these disadvantages, depending on the process, however, it is expedient to optimize the geometry of the reaction-bearing unit: for instance, it can be advantageous for the process to change the tube diameter or the tube length when, for example, an improved catalyst is used. The invention relates to a device serving as reactor for carrying out exothermic chemical reactions which consists of a housing and a reaction-bearing unit, by means of technical detail solutions the entire reactor taking into account the requirements of functionality, pressure and temperature. In a particular embodiment, the ducts of the reaction-bearing unit inlet or outlet lines through the housing wall are supplemented by load-bearing units.

These serve firstly for anchoring the reaction-bearing unit in the housing via a load-bearing support duct, secondly they serve for intercepting stresses occurring in the reactor, in particular heat stresses, which originate from the heating and cooling of the reaction-bearing unit.

The reaction-bearing unit is exchangably installed by the arrangement of a main flange joint in the upper third of the housing (reactor hood), by which this can be separated from the residual housing.

Depending on the requirements of the reaction technique for exothermic reactions, in each case the most suitable reaction-bearing unit, for example in the form of an arrangement of tubes, plates or one or more stages (bundled tubes or plates) can be exchangably used. This unit is preferably introduced into the reactor shell so as to be suspended or to stand. The housing-filling reaction-bearing unit can consist of a plurality of modules which are mounted next to one another and/or one below the other. The number n of these modules can be up to 10.

The reactor underlying the invention is suitable in particular for carrying out exothermic and highly exothermic reactions in which the feedstock gas is brought to reaction in the presence of a heterogeneous catalyst. For example, the apparatus is suitable for the exothermic reaction of methanol with H2S to give methylmercaptan.

The apparatus is likewise particularly suitable for reacting, for example, a C3 component at elevated temperature over a heterogeneous mixed-oxide catalyst with oxygen, steam and/or an inert gas, or preferably an exhaust gas from the reaction from which the condensable components have been separated off.

Furthermore, the construction of the reactor housing is characterized in that, in contrast to conventional tube-bundle reactors, the reaction space, designed as pressure space, co-encloses the cooling space. Thus, in the event of a conceivable leak between two spaces, contamination of the outer region cannot occur.

A part of the inventive concept is the rapid exchangeability of the reaction-bearing unit.

As shown in FIG. 1 to illustrate the invention, one embodiment of the invention consists of a reactor housing which is connected via a load-bearing unit to the reaction-bearing unit. The reaction-bearing units can be anchored to the reactor housing as to be suspended or stand, so that depending on the arrangement the upper or lower side of the reaction-bearing unit in the event of heat stresses can expand or contract. The reactor shell is equipped with a load-bearing unit in such a manner that it is situated on the inside of the reactor shell or on the outside of the reactor shell at the duct of the inlet or outlet lines. The load-bearing unit is able to take up the expansion or contraction of the reaction-bearing unit and as a result compensate for the stresses at the ducts of the reactor shell.

Various types of embodiments of such a compensator are described in the literature. Thus, for example EP 0895806 and EP 1048343 A2 describe compensation of the stresses by the principle of folding. Another embodiment is that the inlet or outlet lines are run in curved form and thus in sufficiently elastic form (see FIG. 2).

The invention further relates to an arrangement of the reaction-bearing unit which is advantageously fixed to the reactor hood in a suspended position. For example, by arranging a main flange joint in the upper region of the housing (reactor hood), preferably in the upper third, a rapid change of reaction-bearing units in total or in parts can be carried out.

The device underlying the invention is suitable in particular for carrying out exothermic and highly exothermic reactions in which a gas phase is passed over a solid material bed and brought to reaction.

This reaction can be, for example, the reaction of methanol with H2S to form methylmercaptan which proceeds under heterogeneous catalysis at elevated pressure and temperature with exothermic heat development.

The apparatuses/devices are particularly suitable for reacting a C3 component, such as, for example, propane or propene, at elevated temperature over a heterogeneous mixed-oxide catalyst with oxygen, steam and/or an inert gas, or preferably an exhaust gas from the reaction from which the condensable components have been separated off. The temperature of the reaction can be up to 600° C. Preference is given to reaction temperatures of 250 to 600° C. The reaction gas should generally have a specific gas velocity GHSV of 500-5000 $h^{-1}$ (gas flow in [l/h]/catalyst volume [l]) and can be brought to reaction at a pressure up to 50 bar absolute. The formulation of the catalyst is not limited. The catalyst can be used, for example, as extrudate, as powder or as supported active composition.

ABBREVIATIONS IN THE FIGURES

1 Compensator
2 Reaction-bearing unit

3 Process gas inlet
4 Process gas outlet
5 Cooling medium, inlet
6 Cooling medium, outlet

Figure 1:
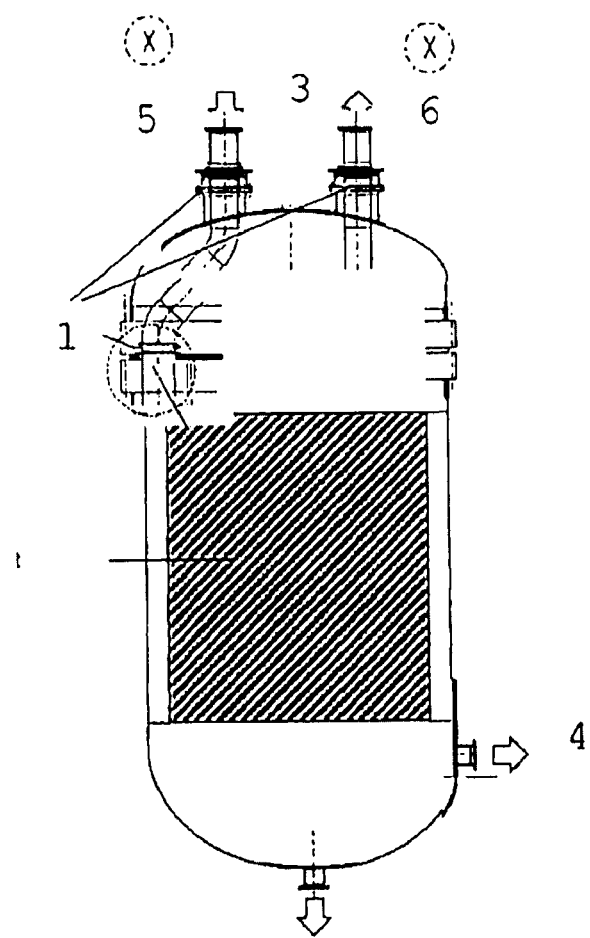
FIG. 1 shows an overall picture of a device according to the invention.
Figure 2:
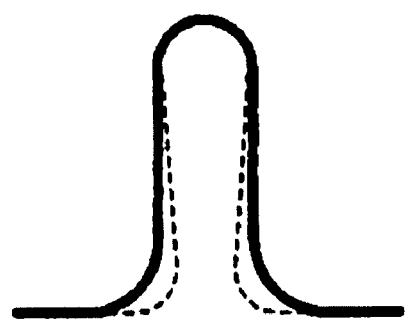
FIG. 2 shows one variant of a compensator according to the invention.
Figure 3:
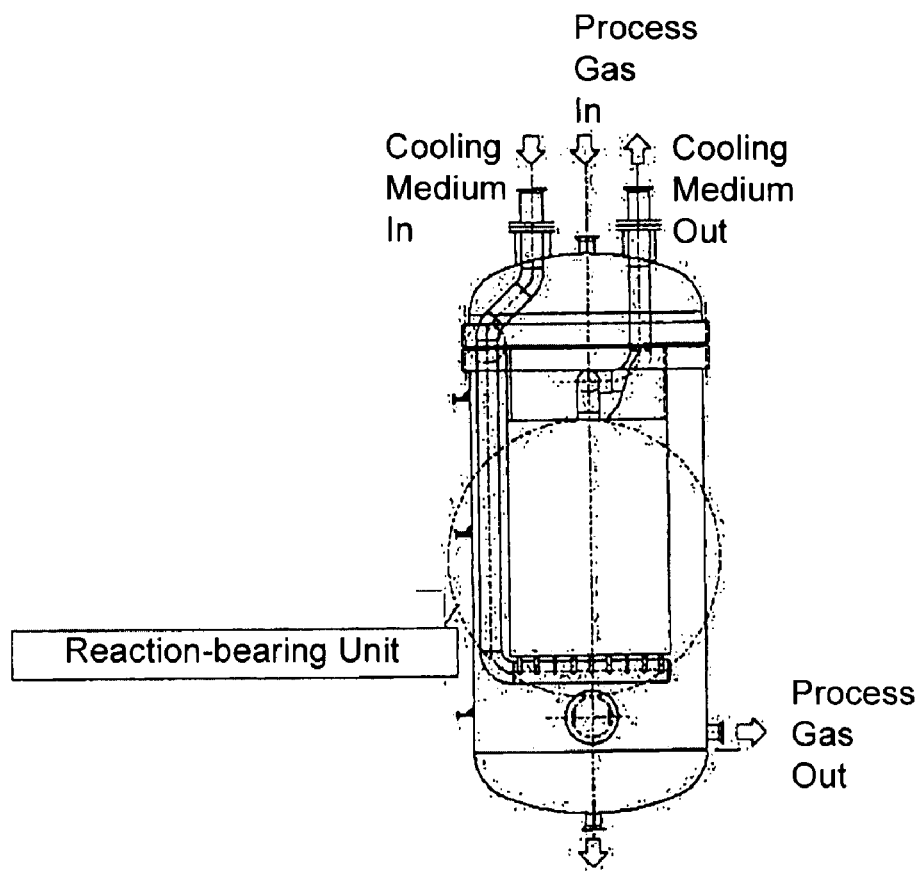
FIG. 3 shows an image of a device showing an embodiment of a reaction-bearing unit within a housing.

The invention claimed is:

1. A device, comprising:
a housing; and
a reaction-bearing unit exchangeable in total or in parts by an arrangement of a main flange joint in an upper third of the housing,
wherein the reaction-bearing unit is mounted in a reactor shell inside said housing so as to be suspended, and
wherein the device is suitable carrying out an exothermic chemical reaction.

2. The device according to claim 1, wherein the reaction-bearing unit comprises a plurality of modules, and wherein the number of the modules is no greater than 10.

3. The device according to claim 2, wherein the modules are mounted next to one another or one below the other.

4. The device according to claim 1, wherein the reaction-bearing unit is inserted into the housing from the top.

5. The device according to claim 1, wherein a reaction space, designed as a pressure space, co-encloses a cooling space.

6. The device according to claim 1, wherein the reaction-bearing unit is formed by an arrangement of tubes, plates or one or more stages.

7. The device according to claim 1, wherein the reaction-bearing unit is fixed to a reactor hood in a suspended position.

8. The device according to claim 1, wherein the reaction-bearing unit is connected to the housing by a load-bearing support duct.

9. The device according to claim 1, wherein the arrangement of the main flange joint directly connects the reaction-bearing unit to the housing.

10. The device according to claim 1, wherein the housing is not contacted by reagents.

11. The device according to claim 1, wherein the reaction-bearing unit is arranged such that, with heat stresses, the reaction-bearing unit can expand or contract within the housing without further contacting the housing or ducts.

12. A device, comprising:
a reactor housing; and
a reaction-bearing unit, which is enclosed by a shell such that reagents of a reaction within the reaction-bearing unit do not contact the reactor housing,
wherein the reaction-bearing unit is exchangeable in total or in part by an arrangement of a main flange joint in an upper third of the reactor housing, and
wherein the reaction-bearing unit is suspended inside the reactor housing.

13. The device according to claim 12, wherein the reaction-bearing unit comprises 1 to 10 modules.

14. The device according to claim 13, wherein the modules are mounted next to one another or one below the other.

15. The device according to claim 12 in which the reaction-bearing unit is inserted into the housing from the top.

16. The device according to claim 12, wherein a reaction space, designed as a pressure space, co-encloses a cooling space.

17. The device according to claim 12, wherein the reaction-bearing unit is formed by an arrangement of tubes, plates or one or more stages.

18. The device according to claim 12, wherein the reaction-bearing unit is fixed to a reactor hood in a suspended position.

19. The device according to claim 12, wherein the reaction-bearing unit is connected to the housing by load-bearing support duct.

\* \* \* \* \*